US006971059B1

(12) United States Patent
Knipe, Jr. et al.

(10) Patent No.: US 6,971,059 B1
(45) Date of Patent: Nov. 29, 2005

(54) CHROMATOGRAPHIC OR SPECTROSCOPIC REPORTS WITH HYPERLINKS TO ALLOW DIRECT ACCESS TO EXTERNAL REFERENCES

(75) Inventors: Charles Robert Knipe, Jr., Collegeville, PA (US); Harriet Patricia Snipes, Wilmington, DE (US)

(73) Assignee: Agilent Technologies, Inc., Palo Alto, CA (US)

( * ) Notice: Subject to any disclaimer, the term of this patent is extended or adjusted under 35 U.S.C. 154(b) by 928 days.

(21) Appl. No.: 09/723,593

(22) Filed: Nov. 28, 2000

(51) Int. Cl.[7] .......................................... G06F 17/00
(52) U.S. Cl. ..................................... 715/500.1; 707/10
(58) Field of Search ........................... 715/501.1, 513, 715/500.1; 707/1, 3, 10; 73/23.35, 23.41; 702/23, 27, 28, 30, 31, 32, 85; 436/161

(56) References Cited

U.S. PATENT DOCUMENTS

| | | | | |
|---|---|---|---|---|
| 5,978,804 | A * | 11/1999 | Dietzman ..................... | 707/10 |
| 6,009,459 | A | 12/1999 | Belfiore et al. ............. | 709/203 |
| 6,025,837 | A | 2/2000 | Matthews, III et al. ..... | 345/327 |
| 6,098,081 | A | 8/2000 | Heidorn et al. ............. | 707/501 |
| 6,125,384 | A | 9/2000 | Brandt et al. ............... | 709/203 |
| 6,240,374 | B1 * | 5/2001 | Cramer et al. ................ | 703/11 |
| 6,323,852 | B1 * | 11/2001 | Blower et al. .............. | 715/804 |
| 6,456,955 | B1 * | 9/2002 | Andrews et al. ............ | 702/104 |
| 6,553,317 | B1 * | 4/2003 | Lincoln et al. ............... | 702/20 |
| 6,606,566 | B1 * | 8/2003 | Sunshine ..................... | 702/22 |
| 6,651,058 | B1 * | 11/2003 | Sundaresan et al. ........... | 707/6 |
| 6,675,166 | B2 * | 1/2004 | Bova ........................... | 707/10 |
| 6,745,204 | B1 * | 6/2004 | Hogue et al. ............. | 707/104.1 |

OTHER PUBLICATIONS

"Associates and CAS sign Pact to Widen Access to Databases", Jan. 1992, Worldwide Videotex, pp. 1-2.*

Lemay, Laura, "Teach Yourself Web Publishing with HTML 3.2 in 14 Days"—Chapter 4 All About Links, 1996, Sams. net Publishing, pp. 77-79.*

Wang, Frank Cheng-Yu, "An HTML Approach to Creating and Maintaining a Chromatography Database", Nov. 1997, Analytical Chemistry, pp. 1-9.*

* cited by examiner

*Primary Examiner*—Sanjiv Shah

(57) ABSTRACT

For chromatographic or spectroscopic data analysis, a method may be created by a developer or expert that contains instrument parameters for a particular sample to control a chromatographic or spectroscopic instrument. A report may then be generated, the content of which may be based upon the processing of data or signal by the method. Hyperlinks or other meta language tools may be inserted by the developer or expert into the data analysis method to direct an operator to an appropriate location, without the operator needing to know anything either about the sample or the location to which he or she is directed. Accordingly, the operator may access a vast amount of information without the need to know the location of the information or going outside the report.

20 Claims, 2 Drawing Sheets

CHROMATOGRAPHIC OR SPECTROSCOPIC REPORTS WITH HYPERLINKS TO ALLOW DIRECT ACCESS TO EXTERNAL REFERENCES

BACKGROUND OF THE INVENTION

The present application relates to improvements in scientific equipment and, in particular, to inclusion of meta language tools within software packages for use with chromatography or spectroscopy.

For chromatographic data analysis, a developer or expert typically creates a method that contains instrument parameters for a particular sample to control a chromatographic instrument. Once the method is created, the sample is "run" using settings in the method to produce peaks, and a report may be generated. The content of the report is based upon the processing of data or signal by the data analysis method.

A calibration table may be used to provide additional information about a particular peak. The information contained in the calibration table generally describes parameters used to identify the peak. However, an operator may need additional information about a particular compound or a peak besides its name. For example, the operator may need additional information about the physical and chemical attributes of a compound or other information relating to a sample being analyzed. To include the additional information as additional fields in the calibration table is prohibitive and generally not expected as part of the chromatographic data analysis package. The additional information may be added using customized reporting solutions, but may require either special software packages or programming by the report developer. Also, the operator may be required to utilize another software application when accessing the report.

Currently, software suppliers and operators may append and embed additional information in a final report by generating a custom report with hyperlinks. With the advent of the world wide web (WWW) and the use of browser technology, many operators are familiar with using hyperlinks to access the additional information from the final report. However, the operator must be quite knowledgeable about the compound or know the source location of the information to access the additional information efficiently from the WWW.

SUMMARY

A method for inclusion of hyperlinks or other meta language tools within a chromatography or spectroscopy software package includes creating a method that controls data analysis parameters used to identify compounds, creating a calibration table that contains the data analysis parameters, processing the data or signal associated with the parameters by the method, and generating a report that provides quantitative and qualitative results of the data or signal processing. The method may further include incorporating meta language tools in the calibration table. The meta language tools link the report to databases or other resources, such as memory or hyperlink locations, that store relevant information relating to the compounds, so that an operator may be directed to the resources without the need to know the location of the resources or go outside the report.

DESCRIPTION OF THE DRAWINGS

The detailed description will refer to the following drawings, in which like numbers refer to like elements, and in which.

DETAILED DESCRIPTION

Figure 1:
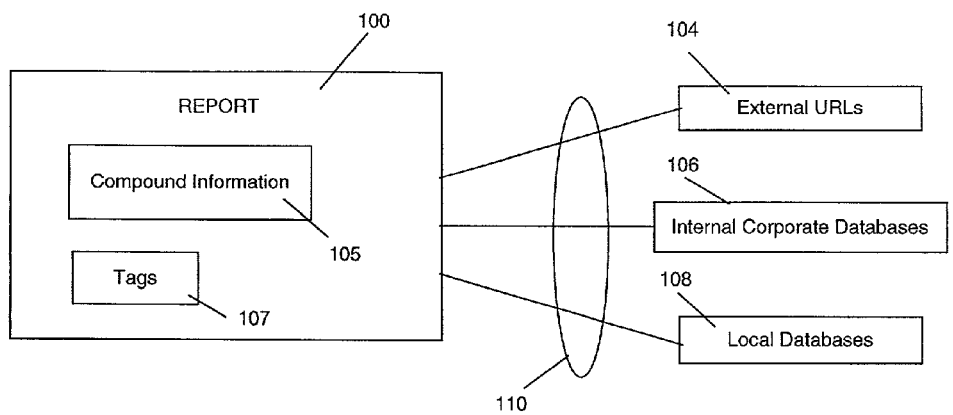
FIG. 1 illustrates a chromatographic report with embedded links directed to various information source locations.

Chromatography is a process in which a chemical mixture carried by a liquid or gas is separated into components as a result of differential distribution of the solutes as they flow around or over a stationary liquid or solid phase. Spectroscopy is a process or technique of using a spectrometer, an instrument for forming and examining spectra especially in the visible region of the electromagnetic spectrum. Both techniques can generate reports containing compound specific information. In the following discussion only the chromatographic system is described in detail. However, the meta language tools may apply to both chromatographic and spectroscopic reports equally and more generally scientific equipment.

In a chromatography system, a sample may be injected or inserted into a chromatographic instrument. A developer or expert may create a method that contains data analysis parameters, such as pressure, temperature, column type for a gas chromatography, or other parameters, to control the instrument. Based on the instrument parameters, the sample may be separated into constituent parts. As the sample constituents passes through a chromatographic column in the instrument, a detector may respond to the sample constituents as the constituents exit the column. The detector response may be displayed as an offset relative to a baseline and may produce peaks in a chromatogram.

If the data or signal is analyzed by itself, certain quantitative information, such as peak retention time, peak width, or peak area, may be derived. However, to provide additional information about what each peak may be and specific information about a particular peak, a calibration table may be used. The calibration table is part of the data analysis portion of the system. The information contained in the calibration table may describe the data analysis parameters for identifying the peak and describing how the peak information may be used in additional calculations. Table 1 shows a portion of a typical calibration table.

TABLE 1

| | Signal | Compound Name | Level | Amount | Retention Time (min) | Response (Area) | Response Factor | Use default Curve |
|---|---|---|---|---|---|---|---|---|
| 1 | 1 | n-pentadecane | 1 | 1.000 | 0.250 | 1.00000 | Yes | Linear |
| 2 | 1 | p-xylene | 1 | 1.000 | 0.750 | 1.00000 | Yes | Linear |
| 3 | 1 | butylbenzene | 1 | 1.000 | 1.750 | 1.00000 | Yes | Linear |
| 4 | 1 | 2-methylpent | 1 | 1.000 | 2.250 | 1.00000 | Yes | Linear |
| 5 | 1 | 2-methybutane | 1 | 1.000 | 3.250 | 1.00000 | Yes | Linear |

The method created by the developer or expert may also describe how to analyze the data or signal generated by the detector. The data analysis may affect how the peaks may be interpreted and quantified. Typically, the developer or expert may analyze a representative sample and generate a report that provides quantitative and qualitative results. These results may be based upon inherent processing algorithms and additional capabilities provided by the information contained in the calibration table. The method settings, including instrument settings and data analysis settings, may be edited, and the sample may be analyzed again. Table 2 shows a typical report.

TABLE 2

| Peak # | Retention Time (min) | Type | Width (min) | Area (counts*s) | Area % | Name |
|---|---|---|---|---|---|---|
| 1 | 0.250 | BP | 0.125 | 987.47973 | 31.22184 | n-pentadecane |
| 2 | 0.750 | BP | 0.125 | 97.54479 | 3.08809 | p-xylene |
| 3 | 1.750 | BP | 0.126 | 988.16975 | 31.28368 | butylbenzene |
| 4 | 2.250 | BP | 0.125 | 97.54479 | 3.08809 | 2-methylpent |
| 5 | 3.250 | BP | 0.126 | 987.99972 | 31.27830 | 2-methybutane |

Once the method is created, the method may be saved and made available for use by an operator. The operator typically selects a method that is appropriate for a particular sample to be analyzed. Because of the complexity already associated with the calibration process, it is desirable to minimize the number of fields that the operator needs to enter. To either customize the report or add additional peak information, a special post analysis program may be used. Most chromatographic data system suppliers allow the operator to specify report types, such as Microsoft Excel format or comma separated variable format, so that the operator may manipulate the report using the post analysis program.

Referring to Table 2, a compound name (or other identifier) may be associated with a particular peak. However, the operator may need additional information about a particular compound or a peak besides its name. For example, the operator may need additional information about the physical and chemical attributes of a compound or other information relating to a sample being analyzed. To include the additional information as additional fields in the calibration table is usually prohibitive and generally not expected as part of the chromatographic data analysis package.

Table 3 shows a calibration table utilizing the hyperlink technology.

expert, for example, due to security, i.e., the developer or expert may be the only individual that has access to knowledge of where the meta language tools reference to. Meta language tools include any method of electronically linking information. Examples include hyperlinks and use of URLs to link information.

After selecting a method appropriate for a particular sample to be analyzed, the operator may check if the report generated from the data or signal analysis contains meta language links. If there are meta language links embedded in the report, the operator may select the meta language links and be directed to information that the developer or expert considers as appropriate. For example, if an extremely hazardous material is to produce a peak at 5.1 minutes in the chromatogram, the hyperlink may point to URLs that describe the appropriate handling and disposal for samples containing such material. Also, a company may have confidential internal corporate databases of samples or sample constituents that may be referenced only by internal code numbers.

By placing the hyperlink information directly in the calibration table, the developer or expert may conveniently embed a large amount of additional information within the data analysis package. Also, the operator who has little or no knowledge of the location of such information may directly access the linked information without the need to go outside the report. No additional software or programming knowledge is required from either the developer or expert or the operator.

The calibration table may include tags, which are one type of embodiment of meta language tools. The tags are commands to a program with directions on how to display or interpret the information following the tags. In HyperText Markup Language (HTML), tags may be used to control how information may be displayed, typically by a web browser. For example, a tag may indicate to an HTML

TABLE 3

| | Signal | Compound Name | Level | Amount | Retention Time (min) | Response (Area) | Response Factor | Use default Curve |
|---|---|---|---|---|---|---|---|---|
| 1 | 1 | <a href="a:\x2.html">n-pentadecane</a> | 1 | 1.000 | 0.250 | 1.00000 | Yes | Linear |
| 2 | 1 | <a href="a:\x3.html">p-xylene</a> | 1 | 1.000 | 0.750 | 1.00000 | Yes | Linear |
| 3 | 1 | <a href="a:\x4.html">butylbenzene</a> | 1 | 1.000 | 1.750 | 1.00000 | Yes | Linear |
| 4 | 1 | <a href="a:\x5.html">2-methylpent</a> | 1 | 1.000 | 2.250 | 1.00000 | Yes | Linear |
| 5 | 1 | <a href="a:\x6.html">2-methybutane</a> | 1 | 1.000 | 3.250 | 1.00000 | Yes | Linear |

The developer or expert may insert meta language tools into the method to be accessed by the operator. The meta language tools may be known only by the developer or interpreter that the information following the tag is a picture, image, or remote uniform resource locators (URL)s. Other meta language tools, such as Extensible Markup Language (XML) or Chemical Markup Language (CML), may use tags to control how information may be directed, stored or used in ways as described by a creator of the tags. Tags may also include other types of information or identifiers for linking. In addition, the meta language tools may be modified easily by simply editing the tags in the calibration table. The generated report now appears as shown in Table 4.

TABLE 4

| Peak # | Retention Time (min) | Type | Width (min) | Area (counts*s) | Area % | Name |
| --- | --- | --- | --- | --- | --- | --- |
| 1 | 0.250 | BP | 0.125 | 987.47973 | 31.22184 | n-pentadecane |
| 2 | 0.750 | BP | 0.125 | 97.54479 | 3.08809 | p-xylene |
| 3 | 1.750 | BP | 0.126 | 988.16975 | 31.28368 | butylbenzene |
| 4 | 2.250 | BP | 0.125 | 97.54479 | 3.08809 | 2-methylpent |
| 5 | 3.250 | BP | 0.126 | 987.99972 | 31.27830 | 2-methybutane |

Table 4 illustrates a report with embedded meta language tools utilizing HTML. Additional meta language tools, such as XML and CML, may be utilized as well. Tables 1–4 can be displayed electronically on a display device in screens, web pages, or other formats.

FIG. 1 illustrates a report 100 with embedded links 110 directed to various compound information source locations, such as external URLs 104, which include government laboratories or other public domain websites; internal corporate databases 106 accessed via an intranetwork, the location of which may be known only to the developer or expert; or local databases 108 on the personal computer (PC) or other machine of the developer or expert. The databases or other resources 104, 106 and 108 may store relevant compound information 105, such as detailed description of the physical and chemical attributes of a particular compound. The developer or expert may be the only individual that has access to knowledge of where the meta language tools 110 reside. The developer or expert may incorporate the meta language tools 110 directly in the calibration table using tags 107, so that the operator may directly access the relevant information stored in the databases or other resources 104, 106 and 108 by, for example, "clicking on" or "double clicking on" the embedded tags 107 using a cursor control device. Upon doing so, the operator's web browser can use the embedded link 110 to locate and retrieve the associated information and display it to the operator. Since the tags 107 may be invisible to the operator, the location of the relevant information may be hidden from the operator.

In addition, a knowledgeable operator may modify the meta language tools 110 within the report 100 by simply editing the tags in the calibration table.

Figure 2:
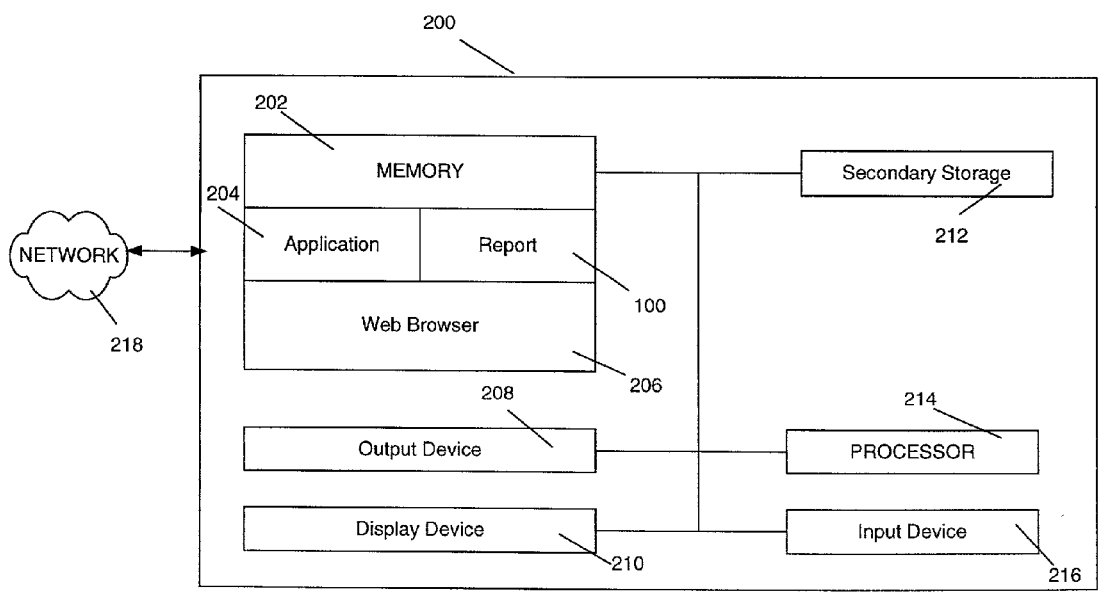
FIG. 2 illustrates exemplary hardware components of a computer that is used to implement the present invention.

FIG. 2 illustrates exemplary hardware components of a computer 200 that is used to implement the present invention. The computer 200 includes a connection with a network 218 such as the Internet or other type of computer or phone networks. The computer 200 typically includes a memory 202, a secondary storage device 212, a processor 214, an input device 216, a display device 210, and an output device 208.

The memory 202 may include random access memory (RAM) or similar types of memory. The memory 202 may store one or more applications 204, including the generated reports 100, for execution by the processor 214. The applications 204 may correspond with software modules to perform processing for the method described below. The memory 202 may be connected to the network 218 by a web browser 206. The web browser 206 makes a connection via the WWW to other computers known as web servers, and receives information from the web servers that is displayed on the computer 200. Information displayed on the computer 200 is typically organized into pages that are constructed using specialized language, such as HTML, XML or CML. The secondary storage device 212 may include a hard disk drive, floppy disk drive, CD-ROM drive, or other types of non-volatile data storage, and it may correspond with various databases or other resources. The secondary storage device 212 may include local databases 108 that may be linked to the generated report 100. The processor 214 may execute applications 204, the generated reports 100, or other information stored in the memory 202, the secondary storage 212, or received from the Internet or other network 218. The input device 216 may include any device for entering data into the computer 200, such as a keyboard, key pad, cursor-control device, touch-screen (possibly with a stylus), or microphone. The display device 210 may include any type of device for presenting visual image, such as, for example, a computer monitor, flat-screen display, or display panel. The output device 208 may include any type of device for presenting data in hard copy format, such as a printer, and other types of output devices include speakers or any device for providing data in audio form. The computer 200 can possibly include multiple input devices, output devices, and display devices.

Although the computer 200 is depicted with various components, one skilled in the art will appreciated that this computer can contain additional or different components. In addition, although aspects of an implementation consistent with the present invention are described as being stored in memory, one skilled in the art will appreciated that these aspects can also be stored on or read from other types of computer program products or computer-readable media, such as secondary storage devices, including hard disks, floppy disks, or CD-ROM; a carrier wave from the Internet or other network; or other forms of RAM or ROM. The computer-readable media may include instructions for controlling the computer 200 to perform a particular method.

Figure 3:
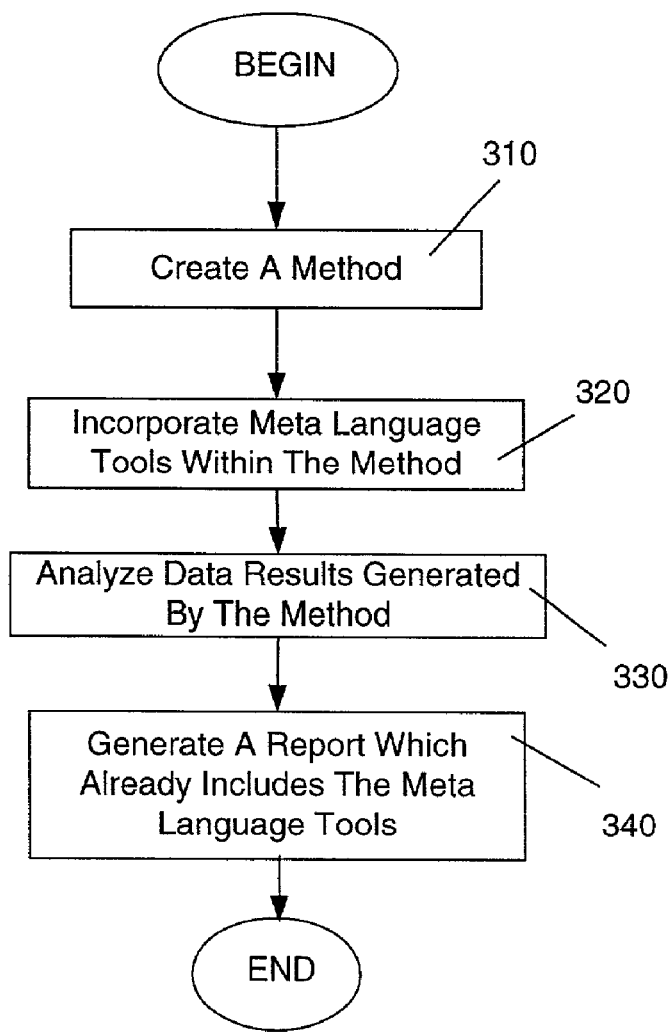
FIG. 3 is a flow chart of a process for incorporating meta language tools within a report generating method.

FIG. 3 is a flow chart of a process for incorporating meta language tools 110 within a report generating method. This method may be implemented with software modules stored in memory 202 for execution by processor 214.

According to current implementation for adding meta language tools in a report, a developer or expert typically creates a method to analyze data results. After the data results are analyzed, an operator may need to call upon an additional software program or software package that add the meta language tools or links. The developer or author of this additional package, which may be the operator, typically would need not only to have knowledge about the location of the meta language tools or links, but also to have sufficient programming skill to insert this information into the report.

According to an embodiment of the present invention, a developer or expert may first create a method that contains data analysis parameters and generates data results for a sample of compounds, step 310. Then the developer or expert may incorporate meta language links 110, such as hyperlink or database references, within the method, step 320. The links may direct an operator to various databases or other resources 104, 106 and 108 that contain information relating to the compounds. In the next step, data results generated by the method are then analyzed, step 330, and a report 100 is created, which already includes the meta language links 110, step 340. The meta language links 110 may utilize HTML, XML, CML, or other programming language. As a result of the process, an operator may access the information stored in the databases or other resources 104, 106 and 108 by simply opening the linked files embedded in the report 100, without the need to know the location of the resources or to go outside the report 100. For example, an operator can "click on" or "double click on" a section having an embedded link using a cursor control device. Upon doing so, the operator's web browser may use the embedded link to locate and retrieve the associated information and display it to the operator. Although the method is described with respect to a developer or expert, others may use it as well to generate reports with embedded links.

While the present invention has been described in connection with an exemplary embodiment, it will be understood that many modifications will be readily apparent to those skilled in the art, and this application is intended to cover any variations thereof.

What is claimed is:

1. A computer readable medium having a program for inclusion of links within a chromatography or spectroscopy software package, the program comprising logic for:
   injecting a sample of compounds into a chromatographic or spectroscopic instrument;
   creating a method that contains data analysis parameters relating to the sample of compounds;
   creating a calibration table that contains the data analysis parameters;
   incorporating meta language tools in the calibration table;
   analyzing the signals generated by the method; and
   generating a report that automatically includes the meta language tools and that provides results of the signal analysis, wherein the metal language tools link the report to resources that store information relating to the compounds, the resources being directly accessible from within the report.

2. The program of claim 1, wherein the incorporating step includes linking uniform resource locators to the report via a network.

3. The program of claim 1, wherein the incorporating step includes linking internal databases to the report.

4. The program of claim 1, wherein the incorporating step includes linking local databases to the report.

5. The program of claim 1, wherein the incorporating step includes using HyperText Markup Language, Extensible Markup Language, or Chemical Markup Language for the meta language tools.

6. The program of claim 1, further comprising using a web browser to display the meta language tools directly in the report.

7. The program of claim 1, further comprising editing the meta language tools in the calibration table.

8. A computer readable medium having a program for inclusion of links within a chromatography or spectroscopy software package, the program comprising logic for:
   creating a method, wherein the method generates data results for a sample of compounds;
   incorporating links within the method, wherein the links direct an operator to resources that contain information relating to the compounds;
   analyzing the data results generated by the method; and
   generating a chromatographic or spectroscopic report that automatically includes the links, wherein the report includes the links embedded within the method, the resources being directly accessible from within the report.

9. The program of claim 8, wherein the incorporating step includes linking uniform resource locators to the report via a network.

10. The program of claim 8, wherein the incorporating step includes linking internal databases to the report.

11. The program of claim 8, wherein the incorporating step includes linking local databases to the report.

12. The program of claim 8, wherein the incorporating step includes using HyperText Markup Language, Extensible Markup Language, or Chemical Markup Language for the links.

13. The program of claim 8, further comprising using a web browser to display the links directly in the report.

14. The program of claim 8, further comprising editing the links in the report.

15. A chromatographic or spectroscopic report, comprising:
   a report stored on a computer-readable medium and generated from a calibration table relating to analysis of samples of compounds, the report including:
   information relating to the compounds; and
   tags automatically included in the report for electronically linking the report to resources that store the information relating to the compounds, the resources being directly accessible from within the report.

16. The report of claim 15, wherein the resources include uniform resource locators that are linked to the report via a network.

17. The report of claim 15, wherein the resources include internal databases accessed via an intranetwork.

18. The report of claim 15, wherein the resources include local databases.

19. The report of claim 15, wherein the tags include HyperText Markup Language, Extensible Markup Language, or Chemical Markup Language.

20. The report of claim 15, wherein the information includes a detailed description of the physical and chemical attributes of the compounds.

* * * * *